United States Patent [19]

Press et al.

[11] Patent Number: 5,192,786
[45] Date of Patent: Mar. 9, 1993

[54] SUBSTITUTED BIPHENYLALKOXYAMINES

[75] Inventors: Jeffery B. Press, Penllyn, Pa.; Pauline Sanfilippo, Flemington, N.J.

[73] Assignee: Ortho Pharmaceutical Corporation, Raritan, N.J.

[21] Appl. No.: 632,274

[22] Filed: Dec. 21, 1990

[51] Int. Cl.$^5$ .................. A61K 31/415; C07D 233/60
[52] U.S. Cl. ................................. 514/399; 548/341.1
[58] Field of Search .......................... 548/341; 514/399

[56] References Cited

U.S. PATENT DOCUMENTS 4,239,767 12/1980 Buckel et al. ....................... 514/399

OTHER PUBLICATIONS

Robertson et al, "Imidazole Anticonvulsants:, etc" *J. Med Chem* (1987) 30, 939-943.

*Primary Examiner*—Patricia L. Morris

[57] ABSTRACT

Novel substituted biphenylalkoxyamines and their synthesis are described. These novel compounds possess antimicrobial activity against yeasts and molds, and also have anticonvulsant and antisecretory properties. The compounds are useful for the treatment of yeast and mold infections in mammals, as well as the treatment of seizures and gastrointestinal diseases in mammals.

9 Claims, No Drawings

SUBSTITUTED BIPHENYLALKOXYAMINES

BACKGROUND OF THE INVENTION

1. Field of the Invention

The present invention relates to novel substituted biphenylalkoxyamines of the formula

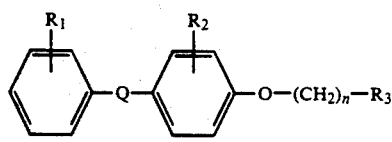

as described further below. These compounds are useful as antimicrobial agents against yeast and mold infections. These compounds also possess anticonvulsant activity and antisecretory activity.

2. Description of the Prior Art

U.S. Pat. No. 4,636,500, issued Mar. 21, 1985, describes N-(phenoxyalkyl)imidazoles of the formula

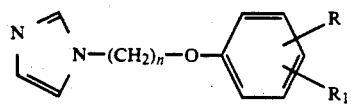

where

R is $OCH_2CO_2R$, $CH_2CONHR$, $OCH_2CONHR$, and $R_1$ is hydrogen, $C_1-C_4$ alkyl, $C_1-C_4$ alkoxy or halogen. These imidazoles are selective inhibitors of the thromboxane synthetase enzyme.

Biphenylalkoxyimidazoles with anticonvulsant properties have been described by Robertson, D. N. et al., J. Med. Chem. 30, 939 (1987). These imidazoles have the following formula

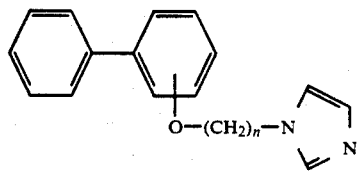

where n is 2, and the side chain is preferably in the ortho position. However, one compound was described in which the side chain was in the para position.

SUMMARY OF THE INVENTION

The present invention is directed to substituted biphenylaldoxyamines of the formula

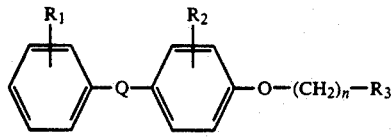

where $R_1$ and $R_2$ may be the same or different, and may be hydrogen, halogen, $C_1-C_6$ alkyl or $C_1-C_6$ alkoxy;

$R_3$ may be $NR_4R_5$, pyrrolidine, piperidine, imidazole or triazole;

$R_4$ and $R_5$ may be the same or different, and may be hydrogen or $C_1-C_6$ alkyl;

Q may be a direct bond, carbonyl, methylene or double bond; and n may be 3-6.

and the pharmaceutically acceptable said addition salts thereof such as, for example, the hydrochloride and the hydrobromide salts.

These compounds are antimicrobial agents which are useful for the treatment of yeast infections and mold infections in mammals. The compounds are particularly useful for the treatment of *Candida albicans* yeast infections and *Trichophyton mentaorophytes* mold infections. These compounds also possess anticonvulsant activity and antisecretory activity, and are therefore also useful for the treatment of seizures and gastrointestinal diseases in mammals.

DETAILED DESCRIPTION OF THE INVENTION

The invention in its broadest aspects relates to substituted biphenylalkoxyamines which have antimicrobial activity against yeast and mold infections in mammals. The substituted biphenylalkoxyamines of the invention which exhibit this antimicrobial activity are shown above.

The preferred compounds of the present invention are those wherein $R_1$ is hydrogen, halogen or $C_1-C_6$ alkoxy;

$R_2$ is hydrogen;

$R_3$ is $NR_4R_5$, imidazole or triazole;

$R_4$ and $R_5$ are propyl;

n is 3-5; and

Q is a direct bond or a double bond.

The compounds of the present invention can be prepared as shown in the following scheme.

SCHEME

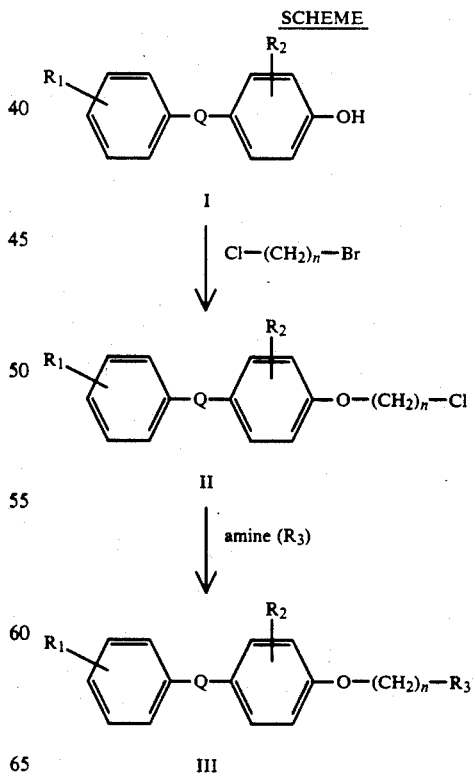

The substituted phenol(I) is treated with a 1-bromo-ω-chloroalkane such as 1-bromo-2-chloroethane, 1- bromo-3-chloropropane, 1-bromo-4-chlorobutane, 1-bromo-5-chloropentane or 1-bromo-6-chlorohexane and a base such as sodium hydride, n-butyllithium, potassium hydroxide or potassium carbonate in a solvent such as dimethylsulfoxide, dimethylformamide, tetrahydrofuran, diethylether, acetone or methanol at a temperature range of 20°-80° C. for 12 to 48 hours. The resultant substituted chloroalkoxyphenyl compound (II) is then treated with an amine such as dimethylamine, diethylamine, dipropylamine, dibutylamine, dipentylamine, piperidine, pyrrolidine, triazole or imidazole in an inert solvent such as benzene, toluene, 2-methoxyethylether or diglyme or neat at 100°-150° C. for 4 to 72 hours to yield the substituted biphenylalkoxyamine (III) of the present invention.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions) or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.5 to about 100 mg/kg, and preferably from about 1 to about 5 mg/kg of the active ingredient.

The following examples describe the invention in greater particularity and are intended to illustrate but not limit the invention.

EXAMPLE 1

(E)-4-(1H-Imidazol-1-yl)butoxystilbene hydrochloride

To a suspension of sodium hydride (60%, 1.5 g, 38 mmol) in 200 ml dimethylformamide was added p-hydroxystilbene (5 g, 25 mmol), portionwise. The mixture was stirred at room temperature for 2 hours and 1-bromo-4-chlorobutane (4.4 mL, 38 mmol) was added. The mixture was then stirred at room temperature overnight. The reaction was quenched with methanol (10 mL) and filtered through Celite ®. The filtrate was taken up in ether (250 mL), washed thrice with water (150 mL) and dried over sodium sulfate. The solution was concentrated to give 8.2 g (75%) of (E)-4-chlorobutoxystilbene as an amber oil. $^1$H NMR (CDCl$_3$): δ7.62–6.81 (m,11H), 4.02 (t,2H), 3.63 (t,2H), 1.99 (m,4H).

A solution of the (E)-4-chlorobutoxystilbene (2.0 g, 7.0 mmol) and imidazole (1.0 g, 14 mmol) in 20 mL of 2-methoxyethyl ether was heated to 120° C. for 24 hours. The solvent was removed by distillation and the resulting residue was chromatographed (flash, SiGel, 9:1 CH$_2$Cl$_2$-MeOH). The hydrochloride salt was made in HCl/MeOH and recrystallized from acetone to give 2.7 g (95%) of the title compound as an off-white solid. m.p. 208°–210° C. IR(KBr): 3400,1590cm$^{-1}$. MS: 319(MH)+. $^1$H NMR(CD$_3$OD): δ9.21(s,1H), 7.65–6.82(m,13H), 4.35(t,2H), 4.02 (t,2H), 2.01(m,4H).

| Anal. Calcd. for | |
|---|---|
| C$_{21}$H$_{22}$N$_2$O.HCl.½H$_2$O: | C, 69.32; H, 6.65; N, 7.70. |
| Found: | C, 69.44; H, 6.63; N, 8.03. |

When in the above procedure, pyrrolidine is used instead of imidazole, then (E)-4-(1H-pyrrolidin-1-yl)butoxystilbene hydrochloride is obtained.

EXAMPLE 2

(E)-4-(1H-Imidazol-1-yl)propoxystilbene hydrochloride

The procedures of Example 1 were followed using 1-bromo-3-chloropropane instead of 1-bromo-4-chlorobutane to give 7.8 g (68%) of (E)-4-chloropropoxystilbene as an amber oil. $^1$NMR (CDCl$_3$): δ7.61–6.80(m,11H), 4.10(t,2H), 3.65(t,2H), 2.12(m,2H).

The title compound was then prepared as described in Example 1 above to give 2.2 g (66%) of (E)-4-(1H-imidazol-1-yl)propoxystilbene hydrochloride as a white solid. m.p. 206°–208° C. IR(KBr): 3310, 1605cm$^{-1}$. MS: 305 (MH+) $^1$H NMR (CD$_3$OD): δ9.01(s,1H), 7.67–6.81(m,13H), 4.50(t,2H), 4.02(t,2H), 2.42(m,2H).

| Anal. Calcd. for | |
|---|---|
| C$_{20}$H$_{20}$N$_2$O.HCl.½H$_2$O: | C, 68.66; H. 6.34; N, 8.00. |
| Found: | C, 68.69; H. 6.73; N, 7.91. |

When in the above procedure, piperidine is used instead of imidazole, then (E)-4-(1H-piperidin-1-yl)propoxystilbene hydrochloride is obtained.

EXAMPLE 3

(E)-3'-Methoxy-4-dipropylamino-propoxystilbene hydrochloride

The procedures of Example 1 were followed using 4-hydroxy-3'-methoxystilbene (5.0 g, 22 mmol) and 1-bromo-3-chloropropane (4.5 mL, 44 mmol) to give 6.1 g (92%) of (E)-4-chloropropoxy-3'-methoxystilbene as an amber oil. $^1$NMR (CDCl$_3$): δ7.51–6.74 (m,10H), 4.11 (t,2H), 3.81 (s,3H), 3.72 (t,2H), 2.22 (m,2H).

The title compound was then prepared as described in Example 1 above using dipropylamine instead of imidazole to give 2.0 g (55%) of (E)-3'-methoxy-4-dipropylaminopropoxystilbene hydrochloride as a white solid. m.p. 181°–182° C. IR (KBr): 2940, 2456, 1600cm$^1$. MS: 368 (MH+) $^1$H NMR (CD$_3$OD): δ7.82–6.90(m,10H), 4.11(t,2H), 3.82(s,3H), 3.26(m,6H), 2.24–1.65(m,6H), 1.03(m,6H).

| Anal. Calcd. for | |
|---|---|
| C$_{24}$H$_{33}$NO$_2$.HCl: | C, 71.35; H. 8.48; N. 3.41. |

| Anal. Calcd. for | |
|---|---|
| Found: | C, 71.49; H, 8.57; N, 3.38. |

When in the above procedure, dibutylamine is used instead of dipropylamine, then (E)-3'-methoxy-4-dibutylaminopropoxystilbene hydrochloride is obtained.

EXAMPLE 4

(E)-3'-Chloro-4-(1H-imidazol-1-yl) propoxystilbene hydrochloride

The procedures of Example 1 were followed using 4-hydroxy-3'-chlorostilbene (5.0 g, 23 mmol) and 1-bromo-3-chloropropane (4.4 mL, 43 mmol) to give 6.1 g (87%) of (E)-4-chloropropoxy-3'-chlorostilbene as an amber oil. $^1$NMR (CDCl$_3$): $\delta$7.66–6.72(m,10H), 4.11(t,2H), 3.72(t,2H), 2.22(m,2H).

The title compound was then prepared as described above in Example 1 to give 1.8 g (53%) of (E)-3'-chloro-4-(1H-imidazol-1-yl)propoxystilbene hydrochloride as an off-white solid. m.p. 185°–186° C. IR (KBr): 1645, 1601cm$^{-1}$ MS: 339 (MH$^+$) H NMR (CD$_3$OD): $\delta$9.11(s,1H), 7.88–6.87(m,12H), 4.11(t,2H), 3.87(t,2H), 2.11(m.2H).

| Anal. Calcd. for | |
|---|---|
| C$_{20}$H$_{19}$ClN$_2$O.HCl: | C, 64.01; H, 5.37; N, 7.46. |
| Found: | C, 64.06; H, 5.36; N, 7.91. |

EXAMPLE 5

(E)-3'-Chloro-4-(1H-imidazol-1-yl) butoxystilbene hydrochloride

The procedures of Example 1 were followed using 4-hydroxy-3'-chlorostilbene (5.0 g, 23 mmol) and 1-bromo-4-chlorobutane (4.5 mL, 43 mmol) to give 6.1 g (87%) of (E)-4-chlorobutoxy-3'-chlorostilbene as an amber oil. $^1$NMR (CDCl$_3$: $\delta$7.66–6.72(m, 10H), 4.11(t, 2H), 3.72(t, 2H), 2.22(m, 4H).

The title compound was then prepared as described above in Example 1 to give 1.3 g (47%) of (E)-3'-chloro-4-(1H-imidazol-1-yl)butoxystilbene hydrochloride as an off-white solid. m.p. 221°–222° C: IR (KBr): 1603, 1573cm$^{-1}$. MS: 353 (MH$^+$). $^1$H NMR (CD$_3$OD): $\delta$9.11(s,1H), 7.88–6.87(m,12H), 4.24(t,2H), 3.87(t,2H), 2.11(m.4H).

| Anal. Calcd. for | |
|---|---|
| C$_{21}$H$_{21}$ClN$_2$O.HCl: | C, 64.79; H, 5.70; N, 7.20. |
| Found: | C, 64.41; H, 5.82; N, 7.41. |

EXAMPLE 6

1-(1H-Imidazol-1-ylbutoxy)-4-phenylbenzene hydrochloride

To a suspension of sodium hydride (60%, 4.7 g, 117 mmol) in dimethylformamide (400 mL) was added 4-phenylphenol (10 g, 60 mmol) portionwise. The mixture was stirred at room temperature for 2 hours, then 1-bromo-4-chlorobutane (13 mL, 117 mmol) was added, and the mixture allowed to stir at room temperature overnight. The reaction was quenched with methanol (30 mL) and filtered through Celite ®. The filtrate was taken up in ether (500 mL), washed thrice with water (250 mL) and dried over sodium sulfate. The solution was concentrated to give 12.2 g (78%) of 4-chlorobutoxy-phenylbenzene as an amber oil. $^1$H NMR (CDCl$_3$): $\delta$7.61–6.88(m.9H), 4.01(t,2H), 3.62(t.2H), 2.01(m,1H).

A solution of the 4-chlorobutoxy-1-phenylbenzene (3.0 g, 11.0 mmol) and imidazole (1.6 g, 22 mmol) in 30 mL of 2-methoxyethyl ether was heated to 120° C. for 24 hours. The solvent was removed by distillation and the resulting residue was chromatographed (flash, Si-Gel, 9:1 CH$_2$Cl$_2$-MeOH). The hydrochloride salt was made in HCl/MeOH and recrystallized from acetone to give 1.5 g (47%) of the title compound as a white solid. m.p. 180°–181° C. IR (KBr): 1605cm$^{-1}$. MS: 293 (MH)$^+$ $^1$H NMR (CD$_3$OD): $\delta$9.11(s,1H), 7.63–6.84(m,12H), 4.50(t,2H), 4.00(t,2H), 1.70(m,4H).

| Anal. Calcd. for | |
|---|---|
| C$_{19}$H$_{20}$N$_2$O.HCl: | C, 69.40; H, 6.44; N, 8.52. |
| Found: | C. 69.52; H, 6.44; N, 8.38. |

EXAMPLE 7

1-(Dipropylaminobutoxy)-4-phenylbenzene hydrochloride

The procedures of Example 6 were followed using dipropylamine instead of imidazole to give 1.6 g (45%) of the title compound as a white solid. m.p. 119°–120° C. IR (KBr): 1605cm$^{-1}$. MS 326 (MH)$^+$. $^1$H NMR (CD$_2$OD): $\delta$7.51–6.80(m,9H), 3.97(t,2H), 2.01(m,6H), 1.72(m,8H), 0.89(m,6H).

| Anal. Calcd. for | |
|---|---|
| C$_{22}$H$_{31}$NO.HCl.¼H$_2$O: | C, 71.23; H, 8.97; N, 3.78. |
| Found: | C, 70.91; H, 9.53; N, 3.77. |

When in the above procedure, diethylamine is used instead of dipropylamine, then 4-phenyl-1-(diethylaminobutoxy)benzene hydrochloride is obtained.

EXAMPLE 8

1-(1H-Imidazol-1-ylpropoxy)-4-phenylbenzene hydrochloride

The procedures of Example 6 were followed using 1-bromo-3-chloropropane instead of 1-bromo-4-chlorobutane to give 1.4 g (37%) of the title compound as a white solid. m.p. 151°–153° C. IR (KBr): 1605cm$^{-1}$. MS: 279 (MH$^+$). $^1$H NMR (CD$_3$OD): $\delta$7.62–6.84(m,12H), 4.51(t,2H), 4.01(t,2H), 2.41(m,2H).

| Anal. Calcd. for | |
|---|---|
| C$_{18}$H$_{18}$N$_2$O.HCl: | C, 68.70; H, 6.09; N, 8.90. |
| Found: | C, 68.77; H, 6.24; N, 8.74. |

EXAMPLE 9

1-(1H-Imidazol-1-ylpentoxy)-4-phenylbenzene hydrochloride

The procedures of Example 6 were followed using 1-bromo-5-chloropentane instead of 1-bromo-4-chlorobutane to give 1.5 g (45%) of the title compound as a white solid. m.p. 166°–168° C. IR (KBr): 1607, 1594cm$^{-1}$. MS: 307 (MH+). $^1$H NMR (CD$_3$OD): δ9.01 (s,1H), 7.81–6.85 (m, 11H), 4.25 (t,2H), 3.99 (t,2H), 1.89 (m,6H).

| Anal. Calcd. for | |
|---|---|
| C$_{20}$H$_{22}$N$_2$O.HCl: | C, 70.06; H, 6.76; N, 8.17. |
| Found: | C, 69.97; H, 6.92; N, 8.19. |

EXAMPLE 10

1-(1H-Triazol-1-ylpentoxy)-4-phenylbenzene hydrochloride

The procedures of Example 6 were followed using 1-bromo-5-chloropentane instead of 1-bromo-4-chlorobutane and 1,2,4-triazole instead of imidazole to give 500 mg (25%) of the title compound as a white solid. m.p. 169°–171° C. IR (KBr): 1607, 1594cm$^{-1}$. MS: 307 (MH+). $^1$H NMR (CD$_3$OD): δ9.19–9.01(2s,2H), 7.81–6.85(m,9H), 4.25 (t,2H), 3.99(t,2H), 1.89(m, 6H).

| Anal. Calcd. for | |
|---|---|
| C$_{19}$H$_{21}$N$_3$O.HCl: | C, 66.36; H, 6.45; N, 12.22. |
| Found: | C, 66.09; H, 6.59; N, 12.25. |

EXAMPLE 11

4'-Chloro-4-(1H-imidazol-1-ylpropoxy) benzophenone hydrochloride

To a suspension of sodium hydride (60%, 1.7 g, 43 mmol) in dimethylformamide (200 mL) was added 4'-chloro-4-hydroxybenzophenone (5 g, 22 mmol) portionwise. The mixture was stirred at room temperature for 2 hours, then 1-bromo-3-chloropropane (4.4 mL, 43 mmol) was added, and the mixture was stirred at room temperature overnight. The reaction was quenched with methanol (10 mL) and filtered through Celite ®. The filtrate was taken up in ether (300 mL), washed thrice with water (150 mL) and dried over sodium sulfate. The solution was concentrated to give 6.1 g (90%) of 4'-chloro-4-chloropropoxybenzophenone as an amber oil. $^1$H NMR (CDCl$_3$): δ7.98–6.89(m,8H), 4.19(t,2H), 3.85(t,2H), 2.29(m,2H).

A solution of the 4'-chloro-4-chloropropoxybenzophenone (3.0 g, 9.7 mmol) and imidazole (1.3 g, 19 mmol) in 2-methoxyethyl ether (20 mL) was heated to 120° C. for 24 hours. The solvent was removed by distillation and the resulting residue was chromatographed (flash, SiGel, 9:1 CH$_2$Cl$_2$-MeOH). The hydrochloride salt was made in HCl/MeOH and recrystallized from acetone to give 1.2 g (36%) of the title compound as a white solid. m.p. 210°–212° C. IR (KBr): 1645, 1601cm$^{-1}$. MS: 341 (MH) . $^1$H NMR (CD$_3$OD): δ9.00(s,1H), 7.89–6.87(m,10H), 4.11(t,2H), 3.45(t,2H), 2.11(m,2H).

| Anal. Calcd. for | |
|---|---|
| C$_{19}$H$_{17}$ClN$_2$O$_2$.HCl: | C, 60.49; H, 4.81; N, 7.43. |
| Found: | C, 60.03; H, 4.81; N, 7.69. |

EXAMPLE 12

1-[4-(1H-Imidazol-1-ylpropoxyphenyl)-1-phenylmethane hydrochloride

To a suspension of sodium hydride (60%, 2.0 g, 49 mmol) in dimethylformamide (200 mL) was added 4-benzylphenol (6.0 g, 33 mmol) portionwise. The mixture was stirred at room temperature for 2 hours, then 1-bromo-3-chloropropane (5.1 mL, 49 mmol) was added and the mixture was stirred at room temperature overnight. The reaction was quenched with methanol (10 mL) and filtered through Celite ®. The filtrate was taken up in ether (300 mL), washed thrice with water (150 mL) and dried over sodium sulfate. The solution was concentrated to give 7.5 g (79%) of 4-chloropropoxyphenyl-1-phenyl-methane methane as an amber oil. $^1$H NMR (CDCl$_3$): δ7.44–6.78 (m,9H), 4.01(t,2H), 3.99(s,2H), 3.55(t,2H), 1.98(m,4H).

A solution of the 4-chloropropoxyphenyl-1-phenylmethane (3.0 g, 11 mmol) and imidazole (1.5 g, 11 mmol) in 2-methoxyethyl ether (20 mL) was heated to 120° C. for 24 hours. The solvent was removed by distillation and the resulting residue was chromatographed (flash, SiGel, 9:1 CH$_2$Cl$_2$-MeOH). The hydrochloride salt was made in HCl/MeOH and recrystallized from acetone to give 2.2 g (68%) of the title compound as a white solid. m.p. 109°–111° C. IR (KBr): 1609cm$^{-1}$. MS 293(MH)+. $^1$H NMR (CD$_3$OD): δ9.00(s,1H), 7.61–6.82(m,11H), 4.11(t,2H), 3.99(s,2H), 3.51(t,2H), 2.20(m,2H).

| Anal. Calcd. for | |
|---|---|
| C$_{19}$H$_{20}$N$_2$O$_2$.HCl.½H$_2$O: | C, 67.55; H, 6.56; N, 8.29. |
| Found: | C, 67.49; H, 6.63; N, 8.28. |

EXAMPLE 13

Pharmacological Activity—In Vitro Antimicrobial Activity

A 0.5 mg/ml stock solution of each Example compound was prepared in an appropriate solvent. From this stock, dilutions were prepared in solvent, and 0.2 ml aliquots of the stock and dilutions were added to tubes containing 19.8 ml of Mueller Hinton agar (46°–50° C.). The mixtures were poured into 100 by 15 mm petri dishes and allowed to solidify.

The test organisms (*Candida albicans* ATC 10231 and *Trichophyton mentagrophytes* ATC 22839) were diluted from frozen stock cultures. Inocula were diluted with sterile solution containing 0.1% peptone in water to contain approximately 2×10$^5$ culture forming units (CFUs) per ml. Plate counts were performed on 1 mL of all inocula.

Each plate and unadulterated agar growth control was inoculated with the inocula prepared above using a Steer's Replicator method. Plates were then incubated at 32° C. Observations for growth were made at 48 hours. The results are reported as the minimal inhibitory concentration (MIC, mcg/ml) which is the lowest concentration of test material which completely inhibits growth.

The results of this test are reported below in Table 1 as compared to the known antifungal agents, miconazole nitrate and terconazole.

TABLE 1

| Example | Minimal inhibitory concentration (mcg/ml) | |
| --- | --- | --- |
|  | Candida albicans | Trichophyton mentagrophytes |
| 1 | >50 | 50 |
| 2 | >50 | 10 |
| 3 | 50 | 50 |
| 4 | >50 | 50 |
| 5 | >50 | >50 |
| 6 | 1 | 1 |
| 7 | 50 | 1 |
| 8 | 1 | 1 |
| 9 | 50 | 10 |
| 10 | >50 | 10 |
| 11 | >50 | 1 |
| 12 | 50 | 10 |
| Miconazole Nitrate | 1 | 5 |
| Terconazole | 0.1 | 50 |

EXAMPLE 14

Pharmacological Activity—In Vitro Antisecretory Activity Isolated Parietal Cell Assay The isolated parietal cell assay was conducted using the procedures of Batzri, S. et al., *Biochemica et Biophysica Acta* 508, 328 (1978) and Soll, A.H. *Am. J. Physiol.* 238, G366 (1980). Basically, parietal cells were isolated from the fundic mucosa of rabbit stomachs by a four-stage collagenase digestion process. The supernatant fractions from the last two stages of this process contain the individual parietal cells. This cell suspension was centrifuged and reconstituted in a modified Hank's buffer to contain $1-2 \times 10^6$ cells/ml. The cells in this suspension were then evaluated for their ability to accumulate $^{14}C$-aminopyrine ($^{14}C$-AP), a weak base which has been shown to accumulate in acidic environments such as the parietal cell. This accumulation was stimulated by histamine and was blocked by $H_2$ antagonists. The cells were incubated with $0.4-0.5 \times 10^6$ cpm $^{14}C$-AP, with various concentrations of histamine as a stimulant, $1 \times 10^{-5}M$ isobutylmethylxanthine, and the test compound added in a 20 µl volume of buffer or DMSO. The flasks were incubated in a shaking water bath at 37° C. for 20 minutes. Two aliquots were then taken from each flask and cell pellets were collected by centrifugation. The pellets were solubilized with Protosol (New England Nuclear) and radioactivity determined by liquid scintillation spectrometry. Data are presented as the $IC_{50}$ vs hist, the concentration of compound required to inhibit $^{14}C$-AP accumulation in the histamine stimulated parietal cell by 50%. The results are shown in Table 2.

When dibutyryl cAMP was used to stimulate the cells instead of histamine, a similar inhibition of $^{14}C$-AP accumulation was measured and the data are presented as the $IC_{50}$ vs cAMP, the concentration of compound required to inhibit $^{14}C$-AP accumulation in the cAMP stimulated parietal cell by 50%.

The results of this experiment are reported below in Table 2 as compared to known antisecretory agents, cimetidine and ranitidine.

EXAMPLE 15

Pharmacological Activity—In Vivo Antisecretory Activity Gastric Secretion

The inhibitory activity of the compounds on acid output was tested using pylorus ligation in a modification of the procedure of Shay, H. et al., *Gastroenterology* 26, 906 (1954). Basically, male Charles River Sprague Dawley derived rats weighing 150-300 grams were deprived of food, but not water, for 18-24 hours prior to use. Water was withheld during the experiment, however. The rats were weighed, anesthetized with ether and the pylorus ligated according to the method of Shay et al., supra. Treatment or vehicle control was then administered intraduodenally (i.d.) or subcutaneously (s.c.). Rats were housed two/cage and sacrificed with $CO_2$ four hours after ligation. The stomachs were removed, rinsed, and contents emptied into a graduated centrifuge tube. The tubes were centrifuged, the volume of gastric juice recorded, and any samples obviously contaminated by feces, food or blood were eliminated. A 1 ml aliquot of gastric juice was titrated with 0.1N NaOH to a pH of 7.0–7.4. The volume of gastric juice secreted, the acid concentration, and the product of the volume times the concentration, i.e., the total amount of acid secreted, were measured. The effect on the acid output by the test compounds compared to the control is shown in Table 2.

The results of this experiment are also reported below in Table 2 as compared to known antisecretory agents, cimetidine and ranitidine.

TABLE 2

| Example | Isolated Parietal Cells ($IC_{50}$, µM) | | Pylorous Ligated Rats (20 mpk, po) |
| --- | --- | --- | --- |
|  | vs his. | vs cAMP |  |
| 1 | 0.45 | 0.45 | −32% |
| 2 | 0.16 | 0.27 | −4% |
| 3 | 0.10 | 0.11 | −92% |
| 4 | 0.34 | 0.40 | NT |
| 5 | 0.18 | 0.10 | −12% |
| 6 | 0.17 | 0.16 | −24% |
| 7 | 0.12 | 0.26 | −45% |
| 8 | 0.23 | 0.32 | −33% |
| 9 | 0.09 | 0.11 | −54% |
| 10 | <10 | <10 | NT |
| 11 | 0.28 | 0.28 | −35% |
| 12 | 0.14 | 0.30 | −51% |
| Cimetidine | 0.82 | >100 | $ED_{50} = 32$ |
| Ranitidine | 0.04 | >100 | $ED_{50} = 6$ |

EXAMPLE 16

Pharmacological Activity—In Vivo Anticonvulsant Activity

Male $CD_1$ mice, fasted at least 16 hours, were divided into groups of 10 and test compounds or vehicle were administered orally by gavage. The vehicle used was 0.5% aqueous methylcellulose solution containing 0.4% (v/v) of Tween 80. One hour later (or at time of suspected peak activity), the mice were challenged with 125 mg/kg of pentylenetetrazol, administered subcutaneously. Pentylenetetrazol was dissolved in 0.9% sodium chloride solution, and the dosage volume for administration of test compounds or the convulsant challenge was 10 ml/kg. Animals were housed individually for observation of convulsions for a period of 30 minutes.

Pentylenetetrazol-induced convulsions in vehicle-treated mice consist of mixed-clonic/tonic seizures. Tonic hindlimb extension and death are terminal consequences. Test compounds that block the hindlimb tonic extensor component of the convulsions in at least 50% of treated mice were considered active. $ED_{50}$ values of active compounds may be calculated by the method of probits (Finney, 1971).

The results of this experiment are shown below in Table 3.

TABLE 3

CNS Pharmacology of a Series of Biphenylalkoxyamines

| Example | General CNS Behavior (Dose mg/kg, p.o.) | Anticonvulsant profile (Dose mg/kg, p.o.) | | | |
|---|---|---|---|---|---|
| | | Antimetrazol | | Antielectroshock | |
| | | (10) | (100) | (10) | (100) |
| 1 | No CNS Activity (100) | NT | − | NT | − |
| 2 | Wk-MOD CNS Stim (100) | − | + | − | + |
| 3 | Wk CNS Depr (10 & 100) | − | + | NT | − |
| 4 | No CNS Activity (100) | NT | − | NT | − |
| 6 | Wk CNS Depr (100) | − | ± | − | ± |
| 7 | CNS/Depr/Stim/Mix (100) | − | ± | − | ± |
| 8 | Wk CNS Depr (100) | − | ± | − | ± |
| 9 | Selective Anti-convulsant | + | + | − | + |
| 11 | Wk/CNS/Depr/Stim (100) | NT | − | NT | − |
| 12 | Mod CNS Depr (100) | − | + | − | + |

Key:
+ Active
± Active, but weak
− Inactive at this dose
NT Dose not tested

What is claimed is:

1. A compound of the formula

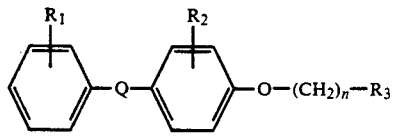

where
R$_1$ and R$_2$ are the same or different and are hydrogen, halogen, C$_1$-C$_6$ alkyl or C$_1$-C$_6$ alkoxy;
R$_3$ is imidazole;
R$_4$ and R$_5$ are the same or different and are hydrogen or C$_1$-C$_6$ alkyl;
Q is a carbonyl, methylene or a vinylene and
n is 3-6, and the pharmaceutically acceptable acid addition salts thereof.

2. The compound of claim 1 wherein
R$_1$ is hydrogen, halogen or C$_1$-C$_6$ alkoxy;
R$_2$ is hydrogen;
R$_3$ is;
R$_4$ and R$_5$ are propyl;
n is 3-5; and
Q is vinylene.

3. The compound of claim 1 selected from the group consisting of (E)-4-(1H-imidazol-1-yl)butoxystilbene hydrochloride, (E)-4-(1H-imidazol-1-yl)propoxystilbene hydrochloride, (E)-3'-chloro-4-(1H-imidazol-1-yl)propoxystilbene hydrochloride, (E)-3'-chloro-4-(1H-imidazol-1-yl)butoxystilbene hydrochloride, 1-(1H-imidazol-1-ylbutoxy)-4-phenylbenzene hydrochloride, 1-(1H-imidazol-1-ylpentoxy)-4-phenylbenzene hydrochloride, 4'-chloro-4-(1H-imidazol-1-ylpropoxy)benzophenone hydrochloride and 1-4-(1H-imidazol-1-ylpropoxyphenyl)-1-phenylmethane hydrochloride.

4. A pharmaceutical composition comprising as an active ingredient an effective amount of the compound of claim 1 and a suitable pharmaceutical carrier.

5. A pharmaceutical composition composition as an active ingredient an effective amount of the compound of claim 2 and a suitable pharmaceutical carrier.

6. A pharmaceutical composition comprising as an active ingredient an effective amount of the compound of claim 3 and a suitable pharmaceutical carrier.

7. A method of treating fungal or mold infections in mammals comprising administering an effective amount of the compound of claim 1.

8. A method of treating fungal or mold infections in mammals comprising administering an effective amount of the compound of claim 2.

9. A method of treating fungal or mold infections in mammals comprising administering an effective amount of the compound of claim 3.

* * * * *